US00PP18877P2

(12) United States Plant Patent
Marten

(10) Patent No.: US PP18,877 P2
(45) Date of Patent: Jun. 3, 2008

(54) ***COLEUS* PLANT NAMED 'MD CURLL06'**

(50) Latin Name: *Solenostemon scutellariodes*
Varietal Denomination: MD CURLL06

(76) Inventor: Walter Marten, Staerrkstr. 19/22, D-16548 Glienicke (DE)

( * ) Notice: Subject to any disclaimer, the term of this patent is extended or adjusted under 35 U.S.C. 154(b) by 132 days.

(21) Appl. No.: 11/395,073

(22) Filed: Mar. 31, 2006

(51) Int. Cl.
*A01H 5/00* (2006.01)

(52) U.S. Cl. ..... Plt./373
(58) Field of Classification Search ..... Plt./373
See application file for complete search history.

*Primary Examiner*—Annette H Para

(57) ABSTRACT

A new and distinct *Coleus* plant cultivar is disclosed, characterized by deeply lobed, undulating leaves, yellow and green foliage, a compact growth habit and short internodes.

1 Drawing Sheet

Latin name of the genus and species: *Solenostemon scutellarioides.*
Variety denomination: 'MD CURLL06'.

BACKGROUND OF THE INVENTION

The new cultivar 'MD CURLL06' was discovered as a naturally occurring whole plant mutation of the parent *Coleus* plant variety 'Bienvenue' (not patented). The new cultivar was discovered in May 2001 as a single plant in a cultivated area of Glienicke, Germany.

Asexual reproduction of the new cultivar 'MD CURLL06' by terminal cuttings was first performed in 2001 in Oxnard, Calif. and has shown that the unique features of this new cultivar are stable and reproduced true to type on successive generations.

SUMMARY OF THE INVENTION

The cultivar 'MD CURLL06' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'MD CURLL06.' These characteristics in combination distinguish 'MD CURLL06' as a new and distinct *Coleus* cultivar:

1. Deeply lobed, undulating leaves;
2. Yellow and green foliage;
3. Compact growth habit; and
4. Short internodes.

Plants of the new cultivar 'MD CURLL06' are similar to plants of the parent variety, 'Bienvenue,' in most horticultural characteristics, however plants of the new cultivar 'MD CURLL06' are much shorter than the parent variety. Also, the leaves of the parent are longer than the new variety. Finally, the foliage of the parent variety was red brown, with yellow-green margins and irregular brown patches on the middle rib while the foliage of 'MD CURLL06' is bright yellow and lime green.

There is no available commercial variety to compare to 'MD CURLL06'.

BRIEF DESCRIPTION OF THE PHOTOGRAPH

The accompanying photograph illustrates in full color a typical plant of 'MD CURLL06' grown in a four-inch pot. One cutting was used in the pot, planted mid December and grown in a greenhouse. During the production of the plants, day temperatures were about 25° C., night temperatures were about 12° C. and light levels ranged from 4,000 to 6,000 footcandles. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 11 week old 'MD CURLL06' plants grown in Oxnard, Ventura County, Calif., during the months of December through February. The growing temperature ranged from 12° C. to 15° C. at night to 12° C. to 20° C. during the day. Measurements and numerical values represent averages of typical *coleus* plants.

Botanical classification: *Coleus* cultivar 'MD CURLL06.'
Commercial classification: *Coleus.*

PROPAGATION

Type cutting: Terminal cuttings.
Time to initiate roots: 4 days with 18° C.
Time to develop roots: 6 to 8 days with 16° C. to 18° C.
Root description: Fine, fibrous, white in color.
Rooting habit: Freely branching.

PLANT

Form: Annual potted or garden plant.
Growth habit: Low and outwardly spreading plant habit.
Growth rate: Moderate.
Plant height: About 10 cm.
Plant diameter: About 13 cm.
Branching habit: Freely branching with about three lateral branches per plant.
Length of lateral branches: About 3 cm.
Diameter: About 0.4 cm.
Internode length: About 0.9 cm.

Strength: Strong.
Aspect: Initially upright then outwardly spreading.
Shape, in cross-section: Squarish.
Texture: Lightly pubescent.
Color: Near Yellow-Green 145A.

FOLIAGE

Arrangement: Opposite; simple.
Length: About 4 cm.
Width: About 4 cm.
Shape: Ovate.
Apex: Broadly acute.
Base: Truncate.
Margin: Crenate.
Texture:
*Upper surface.*—Lightly pubescent.
*Lower surface.*—Lightly pubescent.
Venation pattern: Pinnate; netted.
Color:
*Developing foliage on the upper surface.*—Towards the margins: Near Green 143A. Towards the center: Near Yellow 5B. Center: Near Yellow 5B. Towards the base: Near Yellow 5B. Venation: Near Greyed-Red 180B.
*Developing foliage on the lower surface.*—Towards the margins: Near Green 143A. Towards the center: Near Yellow 5D. Center: Near Yellow 5D. Towards the base: Near Yellow 5D. Venation: Near Yellow 5D.
*Fully expanded foliage on the upper surface.*—Towards the margins: Near Green 143A. Towards the center: Near Yellow 5A. Center: Near Yellow-Green 144B. Towards the base: Near Yellow-Green 144B. Venation: Near Greyed-Red 181D.
*Fully expanded foliage on the lower surface.*—Towards the margins: Near Yellow-Green 144A. Towards the center: Near Yellow 5D. Center: Near Yellow 5D. Towards the base: Near Yellow 5D. Venation: Near Yellow-Green 144C.
Petiole length: About 1 cm.
Petiole diameter: About 0.1 cm.
Petiole color:
*Towards the apex.*—Near Yellow-Green 145B.
*Towards the base.*—Near Yellow-Green 145A.
Flower description: Flower development has not been observed.

OTHER CHARACTERISTICS

Disease resistance: Neither resistance nor susceptibility to diseases or pests has been observed in this variety.
Drought tolerance/cold tolerance: plants of the new *Coleus* have been observed to have no drought tolerance and do not produce at a temperature lower than 8° C.
Fruit/Seed production: Commercially, this plant is not used or observed in a stage where seeds would be produced. Therefore, seed production has not been observed.

What is claimed is:

1. A new and distinct cultivar of *Coleus* plant named 'MD CURLL06' as herein illustrated and described.

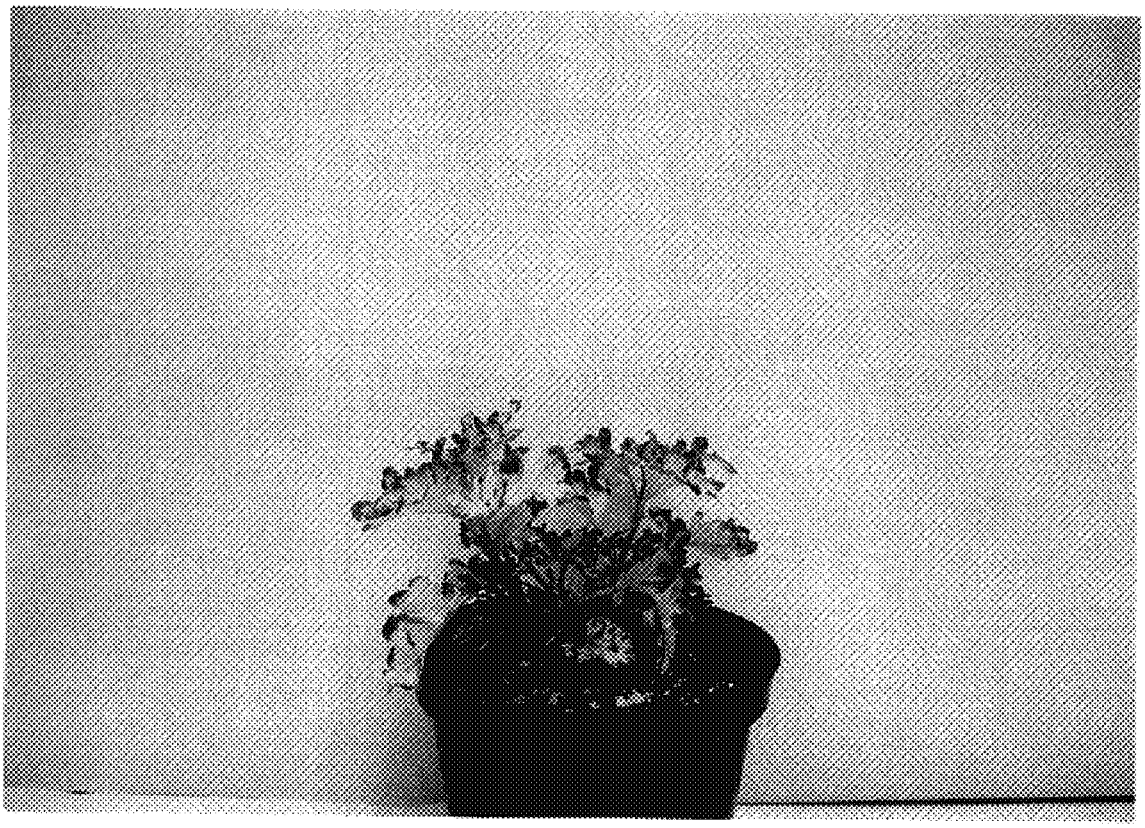

* * * * *